June 4, 1974 R. S. MOORE Plant Pat. 3,563
ROSE PLANT
Filed Jan. 16, 1973
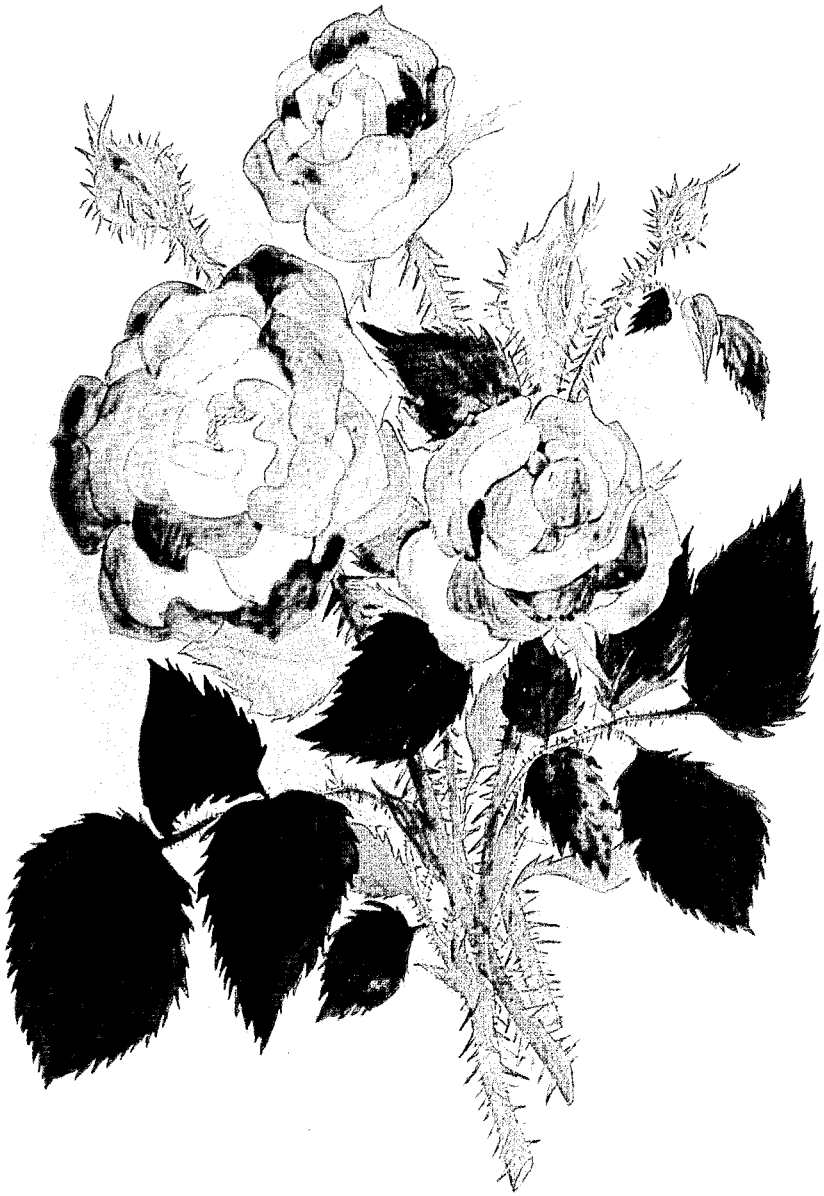

United States Patent Office

Plant Pat. 3,563
Patented June 4, 1974

3,563
ROSE PLANT

Ralph S. Moore, 2519 E. Noble Ave.,
Visalia, Calif. 93277

Filed Jan. 16, 1973, Ser. No. 324,178
Int. Cl. A01h 5/00
U.S. Cl. Plt.—28 1 Claim The present invention relates to a new and distinct variety of hardy, relatively dwarf, bush type rose of the moss class; the variety being primarily characterized—as to novelty—by (a) the buds (calyx) being covered with moss-like extra foliar parts like the old moss rose variety Salet (not patented) and (b) by medium to dark red buds and medium red to orange-red flowers which in general color effect are red to orange-red from opening bud to completely open flower.

The variety is further characterized by:

An abundance of bloom, with flowers borne singly or in loose clusters of 3 to 5.

Moderate to considerable fragrance.

A plant which is vigorous, of bushy upright shape, and with dark green, glossy, fairly large foliage with pointed leaflets; the bud and flower being similar in size and form to a medium or small sized bloom of Baccara (U.S. Plant Pat. 1,367) and the color a shade of red or orange-red similar to Baccara. The plant, which has a normal average height of 2½ to 3 feet at maturity, can easily be maintained at a lower height with occasional trimming.

A plant which grows and blooms satisfactorily both in greenhouse and outdoors and provides excellent garden decoration as well as cut flowers.

The present variety of Moss rose was originated by me at my nursery located at Visalia, California, under conditions of careful control and observation, as a cross between Rumba (U.S. Plant Pat. #1,919), a greenhouse variety, as the seed parent, and an unnamed hybrid moss rose seedling as the pollen parent.

Subsequent to origination of the variety I successfully asexually reproduced it, in my nursery located as aforesaid, by budding as well as by cuttings; the reproductions having run true in all respects.

The figure of the drawing illustrates a spray, including foliage, buds and flowers.

Referring now specifically to the new and distinct variety of moss rose plant, the following is a detailed description thereof in outline; all major color plate identifications being by reference to the British Colour Council Horticultural Colour Chart, except where common terms of color definition are employed.

Type: Hardy; relatively dwarf; bush; seedling; greenhouse; outdoors; cut flowers; garden decoration.
Class: Floribunda moss.

FLOWER

Flowers: Continuity—intermittent to continuous throughout season. Fragrance—quite fragrant.

*Lasting quality.*—Very good.

Flowers borne: Singly and in loose clusters of 3 to 5 on medium length quite stiff stems.

*Quantity of bloom.*—Average both outside and in greenhouse.

*Bud.*—Peduncle—long; slender; wire-like; erect; medium to deep green; numerous thorns and short hairs usually tipped with dark colored ball-like oil glands. Before calyx breaks; size—medium. Form: pointed; with many foliaceous appendages on surface of bud forming finely divided moss-like structures terminating in tiny dark colored ball-like tips (oil glands) and foliaceous parts extending beyond the tips of the bud equal to more than one half of its length. Color—medium green (in greenhouse) with sometimes a bronzy tint. As calyx breaks: color dark red; size—medium. Form—medium length; short pointed. Opening—opens well in all weather.

*Bloom.*—Size when fully open; medium averaging about 2½". Petalage—double—30 to 40 petals arranged regularly. Form—high center at first; later at maturity remaining relatively cupshaped.

*Petals.*—Rather thick; stiff; satiny both inside and outside. Shape: outside petals broad lanceolate (nearly round) with wedge shaped base; intermediate—broad lanceolate (nearly round) with wedge shaped base; inside—similar to intermediate but more narrow.

*Color.*—Newly opened flower from plant grown in plastic house (November 1972) Visalia, Calif.;

*Outside petal.* — Outside surface — Chrysanthemum Crimson 24 (sometimes with darker shadings) blending to yellow at base; inside surface—Currant Red (with darker veining) with small bright yellow area at base.

*Intermediate petal.*—Outside surface—Currant Red 821/3 (sometimes with darker veins) blending to soft then deeper yellow at base; inside surface—Scarlet 19/1 (or darker)—shading to bright yellow at base.

*General color effect newly opened.*—Bright scarlet red to darker. Color is generally darker when grown outdoors.

*Three days open.*—Essentially same orange-red color.

*Behaviour.*—Spent blooms persist for short time then petals drop clean.

*Flower longevity (Fall 1972—in greenhouse).*—5 to 7 days or longer. Outdoors (Fall 1972)—5 to 7 days. Cut flowers at living room temperature—3 to 5 days or longer.

Reproductive organs:

*Stamens.*—Numerous; arranged regularly about pistil.

*Filaments.*—Short to medium yellow.

*Anthers.*—Well formed, yellow.

*Pollen.*—Moderately abundant, yellow.

*Pistils.*—Abundant.

*Styles.*—Medium, bunched, yellow.

*Stigma.*—Yellow.

*Ovaries.*—All enclosed in calyx.

*Hips.*—None.

*Sepals.*—Permanent; spear shaped; covered with moss on outside surface.

*Seeds.*—None.

Foliage:

*Leaves.*—Compound of five leaflets (occasionally 3); abundant; medium to large; leathery; glossy.

*Leaflets.*—Shape: broad lanceolate, nearly oval; apex acute; base rounded; margin serrate. Color: medium to dark green; new growth sometimes tinted bronze (outdoors). Rachis: strong; upper side grooved with a few small hairs or prickles; under side sparsely thorny.

*Stipules.* — Medium long; relatively broad; short points, turning out at an angle of about 45 degrees with numerous tiny hairs along edges.

Growth:

*Habit.*—Bushy; upright; much branched.

*Growth.*—Strong; vigorous.

*Canes.*—Medium to strong.

*Main stems.*—Color: medium green (indoors); green to bronzy or reddish outdoors. Thorns: numerous; slender; medium length; usually straight with sharp points; color—light to medium brown. Some prickles.

*Branches.*—Color: medium green. Thorns: numerous medium length; straight; sharp points; medium length narrow oval base. Prickles—numerous. Hairs—numerous, often ending in oil glands.

The rose plant and its flowers as herein described may vary in slight detail due to climatic, soil and cultural conditions under which the variety may be grown; the present description being of the variety as grown at Visalia, Calif.

The following is claimed:

1. A new and distinct variety of hybrid moss rose plant of hardy, moderately dwarf, much branched, upright, bush type, as illustrated and described, characterized by resemblance to the Baccara rose (U.S. Plant Pat. #1,367) in general form of bud and flower and flower color, the general color effect of the freshly opened flower being an all over orange-red (scarlet red) color of uniform shade, the flowers having good lasting quality both on the plant and as cut flowers; the buds especially characterized by the moss-like appendages consisting of extra foliar parts and small hair-like growths terminating in dark ball-like oil glands; and further characterized by a plant of the floribunda type which is moderately dwarf, much branched, and vigorous in growth, easy to propagate from cuttings and by budding: with medium to large, dark green foliage, an abundance of bloom borne in repeated succession throughout the growing season with flowers borne singly and in loose clusters of 3 to 5 on strong stems.

No references cited.

ROBERT E. BAGWILL, Primary Examiner